(12) United States Patent
Goldberg

(10) Patent No.: US 10,987,072 B2
(45) Date of Patent: Apr. 27, 2021

(54) PORTABLE STERILE C-ARM COVER

(71) Applicant: Grigory Goldberg, Belle Meade, NJ (US)

(72) Inventor: Grigory Goldberg, Belle Meade, NJ (US)

(*) Notice: Subject to any disclaimer, the term of this patent is extended or adjusted under 35 U.S.C. 154(b) by 1 day.

(21) Appl. No.: 16/860,325

(22) Filed: Apr. 28, 2020

(65) Prior Publication Data

US 2021/0077041 A1    Mar. 18, 2021

Related U.S. Application Data

(60) Provisional application No. 62/902,017, filed on Sep. 18, 2019.

(51) Int. Cl.
*A61B 6/00* (2006.01)

(52) U.S. Cl.
CPC ............. *A61B 6/4429* (2013.01); *A61B 6/00* (2013.01); *A61B 6/44* (2013.01); *A61B 6/4423* (2013.01); *A61B 6/4441* (2013.01)

(58) Field of Classification Search
CPC ........... A61B 6/00; A61B 6/44; A61B 6/4423; A61B 6/4429; A61B 6/4441
See application file for complete search history.

(56) References Cited

U.S. PATENT DOCUMENTS

| | | | |
|---|---|---|---|
| 6,619,840 B2 * | 9/2003 | Rasche | A61B 6/032 378/196 |
| 7,108,422 B2 | 9/2006 | Borom | |
| 9,016,282 B2 | 4/2015 | Grajek et al. | |
| 9,307,945 B2 | 4/2016 | Campista | |
| 9,649,077 B2 | 5/2017 | Bouvier et al. | |
| 10,278,659 B2 | 5/2019 | Kim | |
| 2015/0201893 A1 * | 7/2015 | Bouvier | A61B 6/4441 378/62 |
| 2015/0320370 A1 * | 11/2015 | Bouvier | A61B 6/102 378/189 |
| 2016/0038109 A1 * | 2/2016 | Fortuna | A61B 6/4447 378/64 |
| 2018/0289339 A1 * | 10/2018 | Fortuna | A61B 6/0407 |
| 2021/0045829 A1 * | 2/2021 | Bishop | A61B 6/0407 |

FOREIGN PATENT DOCUMENTS

KR    20140138897 A  * 12/2014  ............ H04W 72/04

* cited by examiner

*Primary Examiner* — Anastasia Midkiff
(74) *Attorney, Agent, or Firm* — Fox Rothschild LLP

(57) ABSTRACT

A sterile X-ray imaging C-arm cover is provided. The sterile X-ray imaging C-arm cover includes an enclosure configured to be secured to a medical table and to cover a portion of a C-arm, two sidewalls extending from a rotation end to a bottom end. The enclosure may include a front wall extending between the two sidewalls, enabling a medical professional to move around the enclosure to access a patient on the medical table. The enclosure may include a bottom wall coupled to the front wall and the two sidewalls, wherein the two sidewalls, the front wall, and the bottom wall form an envelope configured to receive the portion of the C-arm. The sterile X-ray imaging C-arm cover may include one or more securing mechanisms configured to secure the C-arm cover to the medical table, wherein the one or more securing mechanisms are positioned at the rotation end of the enclosure.

12 Claims, 4 Drawing Sheets

PORTABLE STERILE C-ARM COVER

CROSS-REFERENCE TO RELATED APPLICATIONS

This application claims priority under 35 U.S.C. § 119(e) to U.S. Provisional Application No. 62/902,017, filed Sep. 18, 2019, the disclosure of which is incorporated herein by reference in its entirety.

TECHNICAL FIELD

The present disclosure relates to covers for maintaining the sterility of medical equipment and, in particular, to a cover for imaging equipment incorporating a C-arm which maintains the sterility of the C-arm and enables medical professionals to access patients while the C-arm is in use.

BACKGROUND

During medical procedures, patients are often positioned on medical tables configured to give medical professionals adequate access to the patients during the medical procedure. The medical professionals, however, are not always able to view necessary areas of the patient's anatomy with the naked eye and require medical imaging equipment to view the areas needed to successfully perform the medical procedures.

Unfortunately, during many medical procedures, it is not possible or practical to perform imaging, e.g., X-ray imaging, on a patient using standard imaging equipment due to the size and shape of certain imaging equipment and the positioning of the patient during the medical procedure. In order to overcome this obstacle, X-ray imaging systems incorporating C-arms are often used during medical procedures in order to image a patient or portions of a patient at angles, positions, and locations where standard imaging equipment would not be possible or practical.

C-arm imaging systems typically incorporate X-ray generators and imaging equipment and, as the name suggests, a C-shaped arm configured to rotate around a fixed axis (typically rotating around a medical table during a medical procedure) and image patients in real-time during medical procedures. While in use, the C-arm typically rotates under and around a medical table on which the medical procedure is performed. By rotating the C-arm around the medical table, the imaging system is capable of imaging the patient or portions of the patient at various angles.

While the C-arm brings with it practically in terms of imaging patients, it also brings with it sterility concerns. Since the C-arm rotates around the medical table, the C-arm comes into close proximity to the patient upon the medical table. This places the C-arm in the position of possibly becoming contaminated by the patient on the medical table. In order to maintain the sterility of the C-arm, covers are used to prevent contact between the patient and C-arm. These covers must maintain coverage of the portion of the C-arm that may come into contact with the patient.

During imaging, it is beneficial for medical professionals to be able to have access to the patient. However, common C-arm covers couple to the medical table along the length of the medical table. In this setup, when the C-arm is inserted into the C-arm cover, the C-arm cover expands at all points along the side of the medical table upon insertion of the C-arm, preventing the medical professionals from adequately accessing the patient while the C-arm is in use. For at least this reason, a C-arm cover configured to maintain the sterility of the C-arm while being configured to enable the medical professional to have adequate access to the patent is needed.

SUMMARY

The present invention fills the foregoing need by providing an advantageous sterile X-ray imaging C-arm cover. The sterile X-ray imaging C-arm cover includes an enclosure configured to be secured to a medical table and to cover a portion of a C-arm. The enclosure may include two sidewalls extending from a rotation end to a bottom end, a width of each of the two sidewalls increasing to a desired width from the rotation end to the bottom end. The enclosure may include a front wall extending between the two sidewalls, wherein the front wall has a width greater than a width of the portion of the C-arm while enabling a medical professional to move around the enclosure to access a patient on the medical table. The enclosure may include a bottom wall coupled to the front wall and the two sidewalls, wherein the two sidewalls, the front wall, and the bottom wall form an envelope configured to receive the portion of the C-arm. The sterile X-ray imaging C-arm cover may include one or more securing mechanisms configured to secure the C-arm cover to the medical table at a position configured to enable the enclosure to receive the portion of the C-arm, wherein the one or more securing mechanisms are positioned at the rotation end of the enclosure.

In some embodiments, the one or more securing mechanisms are configured to enable the C-arm cover to rotate around the one or more securing mechanisms, enabling the C-arm cover rotate around the surgical table upon receiving the portion of the C-arm within the enclosure.

In some embodiments, the one or more securing mechanisms are selected from the group consisting of one or more mechanical clamps, one or more hook and loop fasteners, one or more adhesive strips, and one or more snap fasteners.

In some embodiments, the enclosure includes plastic.

In some embodiments, at least a portion of the enclosure is collapsible, forming a collapsible portion. In some embodiments, the collapsible portion is configured to expand to an expanded shape upon insertion of the portion of the C-arm into the envelope formed by the enclosure.

In some embodiments, the enclosure is rigid in shape, wherein the rigid shape has a width greater than that of the portion of the C-arm.

In some embodiments, the width of the front wall is fixed at a width greater than a width of the portion of the C-arm. The width of the front wall may alternatively be variable along the length of the front wall.

In some embodiments, the bottom wall has a height equal to a maximum width of the two sidewalls.

In some embodiments, the one or more securing mechanisms are removable from the medical table, enabling the C-arm cover to be repositioned along the medical table to accommodate the portion of the C-arm.

In some embodiments, the front wall and the bottom wall are a singular component.

DETAILED DESCRIPTION

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" (or "comprises") means "including (or includes), but not limited to." When used in this document, the term "exemplary" is intended to mean "by way of example" and is not intended to indicate that a particular exemplary item is preferred or required.

In this document, when terms such "first" and "second" are used to modify a noun, such use is simply intended to distinguish one item from another, and is not intended to require a sequential order unless specifically stated. The term "approximately," when used in connection with a numeric value, is intended to include values that are close to, but not exactly, the number. For example, in some embodiments, the term "approximately" may include values that are within +/−10 percent of the value.

Figure 1:
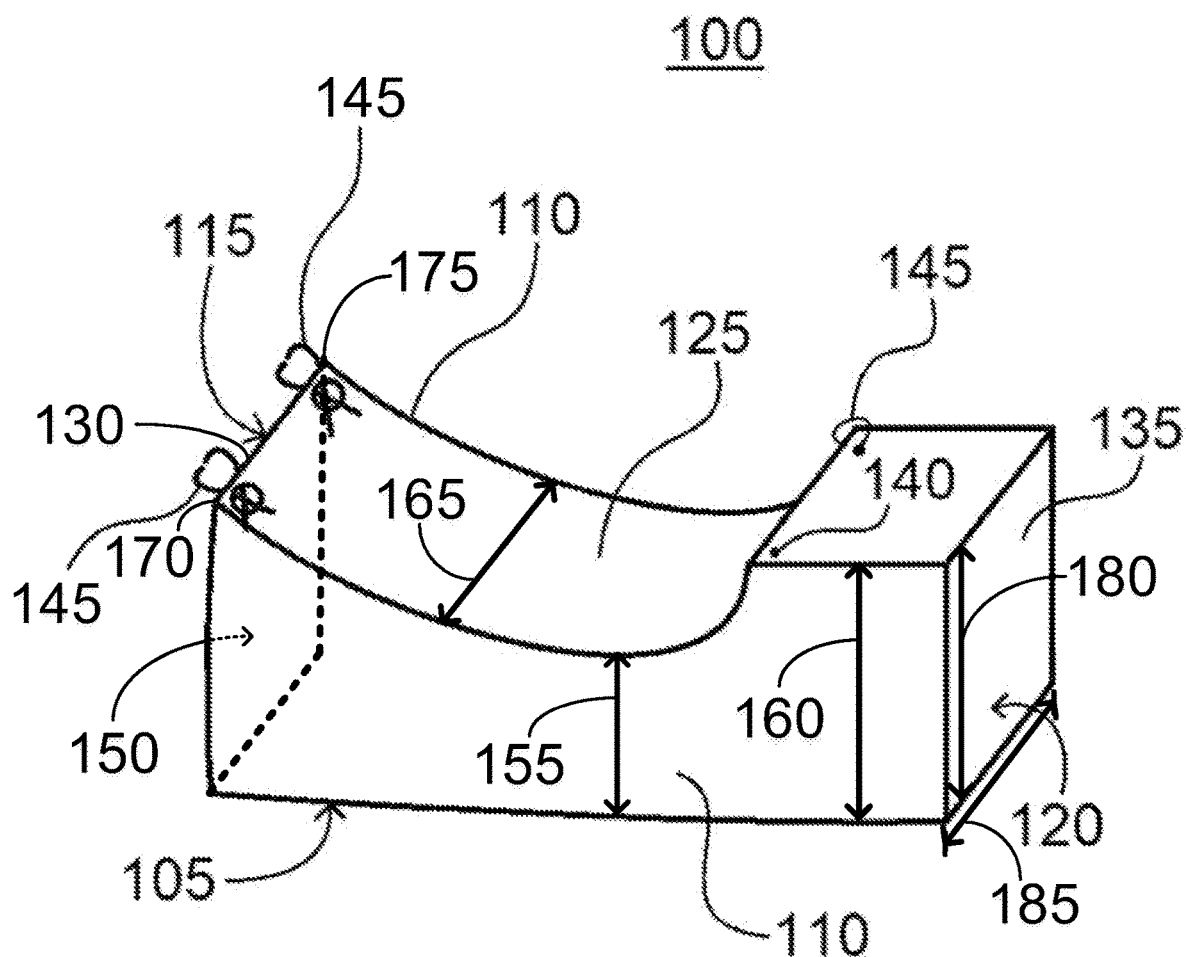
FIG. 1 is a perspective view of an example of a C-arm cover of the present disclosure.

Referring now to FIG. 1, a perspective view of a sterile X-ray imaging C-arm cover 100 for covering a portion of a C-arm are illustratively depicted in accordance with various embodiments presented in the present disclosure.

Imaging systems incorporating C-arms are often used by medical professionals for imaging patients during medical procedures. The C-arm cover 100 as described herein is configured to cover a portion of the C-arm in order to maintain the sterility of the C-arm during use.

Figure 2A:
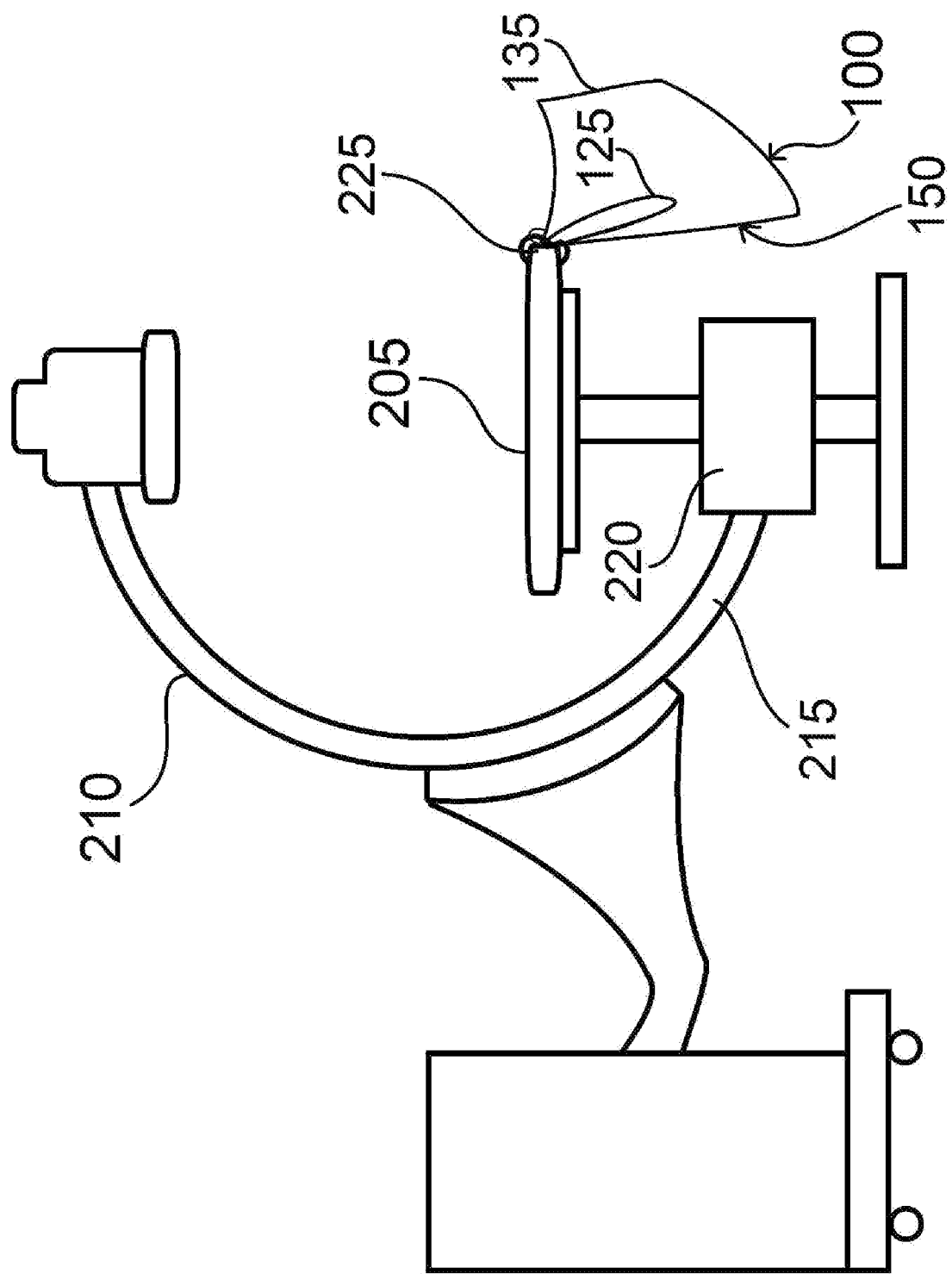
FIGS. 2A-2B are diagrams of an example a C-arm cover of the present disclosure coupled to a medical table in a first position (FIG. 2A) and a second position (FIG. 2B).
Figure 2B:
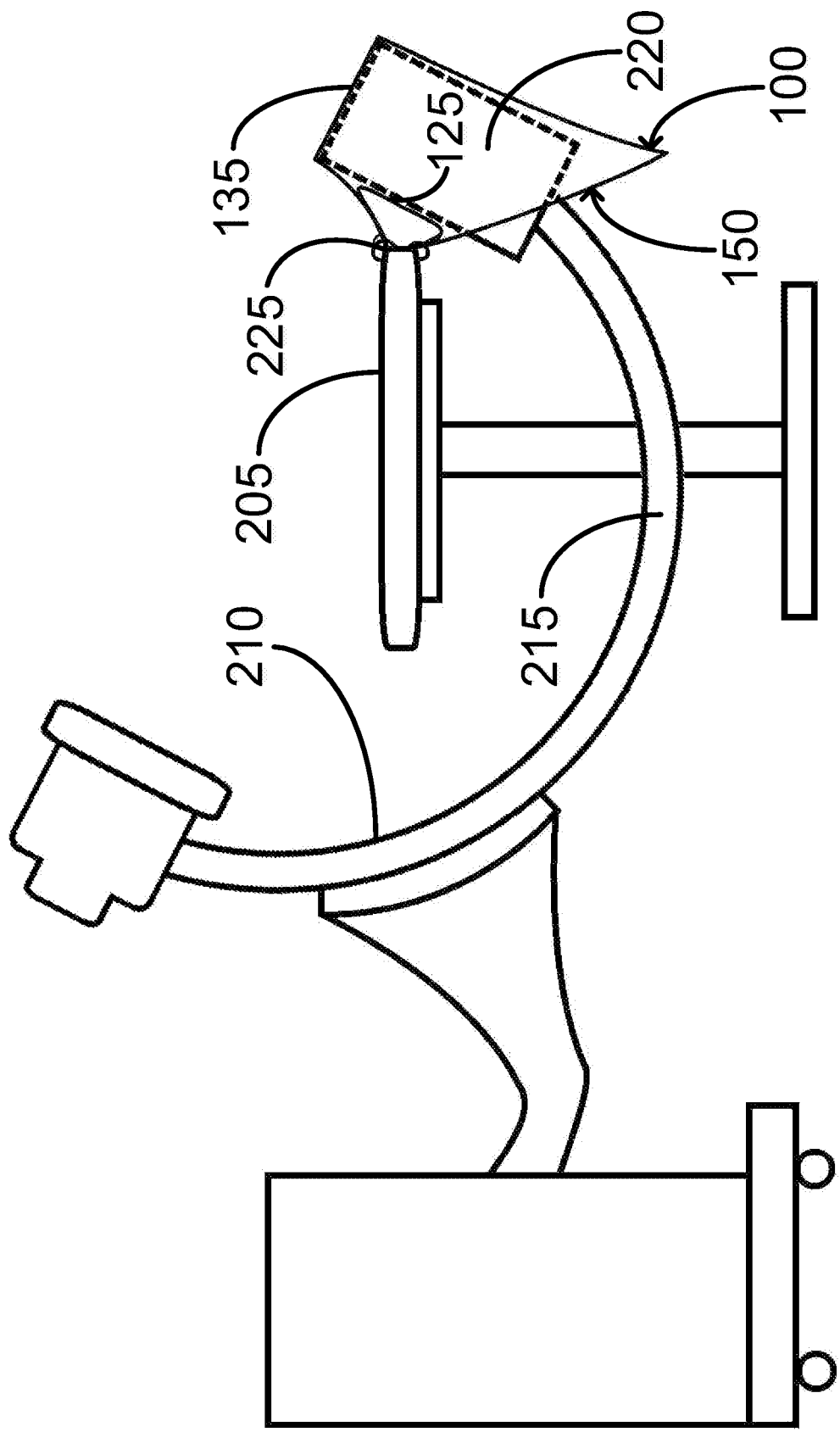
Figure 3A:
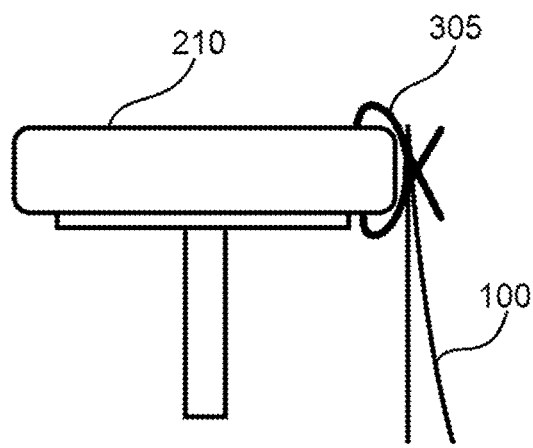
FIGS. 3A, 3B, 3C and 3D are perspective views of examples of various securing mechanisms coupled to the C-arm cover of the present disclosure.
Figure 3B:
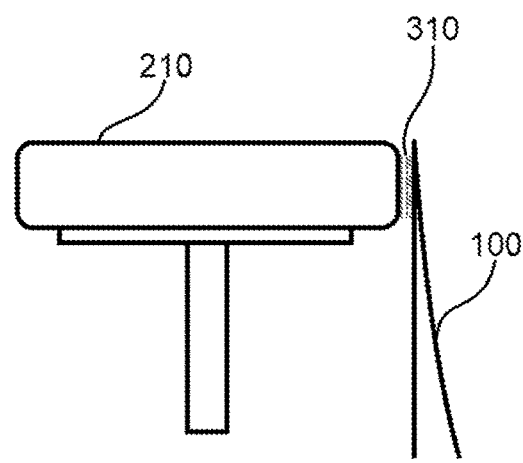
Figure 3C:
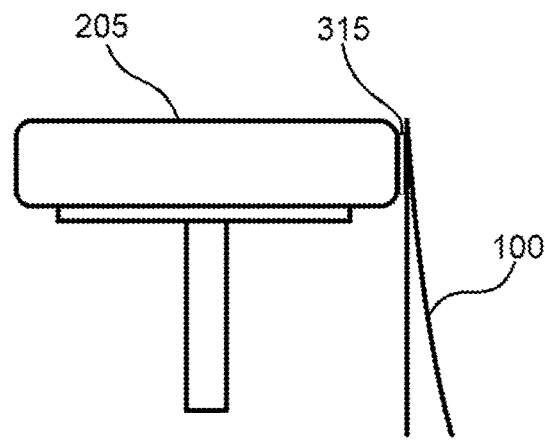
Figure 3D:
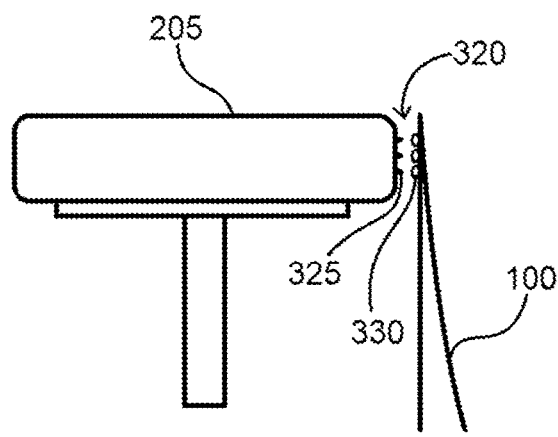

According to various embodiments, the C-arm cover 100 may include an enclosure 105. The enclosure 105 forms an opening 150 and is configured to receive a portion of the C-arm cover through the opening 150 as the C-arm rotates (as shown in FIG. 2B), causing a portion of the C-arm (which may include one or more portions of the curved C-arm 215 and/or a detector 220 affixed to the curved C-arm, as shown in FIGS. 2A-2B) to protrude from under a medical table 205 (as shown, for example, in FIGS. 2A-2B). The enclosure 105 may conform to the shape of the portion of the C-arm being inserted into the enclosure 105. The enclosure 105 may include plastic and/or any other suitable material or materials. The enclosure 105 may include two sidewalls 110 extending from a rotation end 115 of the C-arm cover 100 to a bottom end 120 of the C-arm cover 100. According to various embodiments, each of the sidewalls 110 increases in width from a minimum width 155 a maximum width 160 at the bottom end 120. According to various embodiments, the maximum width 160 is a desired width.

The enclosure 105 may include a front wall 125 extending between the two sidewalls 110 and forming the width of the C-arm cover 100. The front wall 125 may have a width 165 greater than that of a portion of the C-arm over which the C-arm cover 100 is intended to cover, enabling the enclosure 105 to encompass the portion of the C-arm and aid in the prevention of contamination of the C-arm during use. According to various embodiments, the front wall 125 may have a fixed width, resulting the in the C-arm cover 100 having a fixed width. The fixed width is greater than a width of the portion of the C-arm, enabling the C-arm cover 100 to cover the portion of the C-arm. According to various embodiments, the width 165 of the front wall 125 may vary along the length of the front wall 125. According to various embodiments of the present disclosure, the width 165 of the front wall 125, whether fixed or variable, is configured to be greater than a portion of the C-arm being covered by any particular portion of the enclosure 105.

If a width of the C-arm cover were to extend from one end of the medical table to another end of the medical table, upon insertion of the portion of the C-arm, the entire C-arm cover would expand along the length of the medical table. This expansion of the C-arm cover would cause the C-arm cover to prevent the medical professional from accessing the patient which the C-arm and the C-arm cover were in use. This creates a hindrance to the medical professional's ability to adequately examiner and/or perform medical procedures or the patient during use of the C-arm cover.

Due to these hindrances found in typical C-arm covers, the C-arm cover 100 described herein in the present disclosure has a width 165 configured to enable the C-arm enclosure 105 to adequately cover the portion of the C-arm. The width 165 is such as to enable the medical professional to move around the enclosure 105 to access the patient during the medical procedure. This access allows the medical professional to better perform his or her professional duties and makes the medical procedure safer for the patient due to the medical professional's easier access to observe the patient. For at least these reasons, the C-arm cover described herein in the present disclosure improves upon the existing technologies.

According to an embodiment, the rotation end 115 of the C-arm cover 100 includes a retaining mechanism 130 extending from a first end 170 of the front wall 125 to a second end 175 of the front wall 125. The retaining mechanism 130 may provide structural strength, aiding in maintaining the width of the C-arm cover 100. The retaining mechanism 130 may be a bar and/or may include any suitable form capable of providing adequate structural support. The retaining mechanism 130 may include metal, plastic, and/or any other material suitable for use with the C-arm cover 100 and may be coupled directly to the front wall 125 and/or may be inserted into one or more receiving holes. According to various embodiments, the front wall 125 may include one or more securing mechanisms 145 (e.g., string, rope, hook, clip, etc.) for securing a portion of the front wall 125 to one or more of the retaining mechanisms 130. The one or more securing mechanisms 145 may be coupled directly to the front wall 125 and/or may be inserted into one or more holes 140.

The C-arm cover may further include a bottom wall 135. The bottom wall is coupled to the sidewalls 110 and the front wall 125. The bottom wall 135 may have a height 180 approximately equal to the maximum width 160 of the sidewalls 110. Other heights and/or widths 185 of the bottom wall 135 may alternatively be used in various embodiments. The sidewalls 110, front wall 125, and bottom wall 135 form the enclosure 105 into which the portion of the C-arm is to be inserted. According to various embodiments, the front wall 125 and the bottom wall 135 may be a singular piece.

According to various embodiments, the front wall 125 and the bottom wall 135 may be separate pieces.

According to various embodiments, the enclosure 105 may be flexible, either entirely or partially. If the enclosure 105 is partially flexible, the enclosure 105 may be configured to collapse, taking up less room around the medical table when the portion of the C-arm is not inserted into the enclosure 105. The enclosure 105 and/or the collapsible portion may expand upon the insertion of the portion of the C-arm being covered by the enclosure 105. According to various embodiments, the enclosure 105 may be rigid, either entirely or partially, maintaining its general shape whether or not the portion of the C-arm has been inserted into the enclosure 105.

Referring now to FIGS. 2A-2B, diagrams of an example a C-arm cover 100 of the present disclosure coupled to a medical table 205 are illustratively depicted, in accordance with an embodiment of the present disclosure.

The C-arm cover 100 may include one or more securing mechanisms 140 coupled to the rotation end 115 of the C-arm cover 100. The one or more securing mechanisms 140 may be configured to secure the C-arm cover 100 to a portion of the medical table 205, wherein the C-arm cover 100, when secured to the portion of the medical table 205, is positioned such that the C-arm cover 100 enclosure 105 receives a portion of the C-arm 210 as the C-arm 210 rotates around the medical table 205.

According to various embodiments, one or more of the one or more securing mechanisms 140 may include, as shown in FIGS. 3A-3D, mechanical clamps 305 (FIG. 3A), one or more hook and loop fasteners 310 (FIG. 3B), one or more adhesive strips 315 (FIG. 3C), one or more snap fasteners 320 (FIG. 3D), and/or any other suitable form of securing mechanism 140 for securing the C-arm cover 100 to the medical table 205.

The mechanical clamps 305 may be coupled to the enclosure 105. The mechanical clamps 305 may be clamped onto a portion 210 of the medical table 205, enabling the C-arm cover 100 to rotate around the clamps 305, at 225 (as shown in FIGS. 2A-2B), upon insertion of the portion of the C-arm 210 into the enclosure 105.

The hook and loop fasteners 310 may be coupled to the enclosure 105 and the medical table 205, with either the enclosure 105 or the medical table 205 having the hook fastener coupled thereto and the remaining enclosure 105 or medical table 205 having the loop fastener coupled thereto, enabling the C-arm cover 100 to be coupled to the medical table 205 via the connection of the hook and loop fastener 310.

The enclosure 105 may include an adhesive strip 315 coupled thereto. The adhesive strip 315 may enable the C-arm cover 100 to stick to the medical table 205 via the adhesive strip 315.

The snap fasteners 320 may be coupled to the enclosure 105 and the medical table 205, with either the enclosure 105 or the medical table 205 having a cap 325 portion of the snap fastener 320 coupled thereto and the remaining enclosure 105 or medical table 205 having the socket portion 330 of the snap fastener 320 coupled thereto, enabling the C-arm cover 100 to be coupled to the medical table 205 via the connection of the snap fastener 320.

According to various embodiments, the one or more securing mechanisms 140 may be removable from the medical table 205 (as shown, for example, in FIG. 1), enabling the C-arm cover 100 to be repositioned along the medical table 205. This enables the user to reposition the C-arm cover 100 to adequately cover the portion of the C-arm 210 in the event that the C-arm 210 and/or the medical table 205 and/or the C-arm cover 100 have to be moved. One or more of the one or more securing mechanisms 140 may be permanently affixed to the enclosure 105 and/or removably coupled to the enclosure 105. The one or more securing mechanisms 140 may be coupled to the enclosure 105 via mechanical means, via an adhesive, and/or through any other suitable means of coupling the one or more securing mechanisms 140 to the enclosure 105.

According to various embodiments, the C-arm cover 100 is configured to hang down from the one or more securing mechanisms 140 and rotate about the one or more securing mechanisms 140 at the rotation end 115 upon insertion of the portion of the C-arm into the enclosure 105, through the opening 150. By hanging from the one or more securing mechanisms 140, the C-arm cover 100 stays entirely or primarily out of the way of the medical professional while the C-arm portion is not inserted into the enclosure 105. Upon removal of the C-arm portion from the enclosure 105, the C-arm cover 100 rotates about the rotation end 115 and returns to the hanging position against the medical table While certain embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the present disclosure.

What is claimed is:

1. A sterile X-ray imaging C-arm cover comprising:
   an enclosure configured to be secured to a medical table and to cover a portion of a C-arm, the enclosure having:
      two sidewalls extending from a rotation end to a bottom end, a width of each of the two sidewalls increasing from a minimum width to a desired width at the bottom end;
      a front wall extending between the two sidewalls, wherein the front wall defines a width of the enclosure, the width of the enclosure being greater than a width of the portion of the C-arm; and
      a bottom wall coupled to the front wall and the two sidewalls,
         wherein the enclosure is configured to receive the portion of the C-arm; and
   one or more securing mechanisms configured to secure the C-arm cover to the medical table at a position configured to enable the enclosure to receive the portion of the C-arm,
   wherein the one or more securing mechanisms are positioned at the rotation end of the enclosure.

2. The sterile X-ray imaging C-arm cover as recited in claim 1, wherein the one or more securing mechanisms are configured to enable the C-arm cover to rotate around the one or more securing mechanisms, enabling the C-arm cover to rotate around the medical table upon receiving the portion of the C-arm within the enclosure.

3. The sterile X-ray imaging C-arm cover as recited in claim 1, wherein the one or more securing mechanisms include are selected from the group consisting of one or more mechanical clamps, one or more hook and loop fasteners, one or more adhesive strips, and one or more snap fasteners.

4. The sterile X-ray imaging C-arm cover as recited in claim 1, wherein the enclosure includes plastic.

5. The sterile X-ray imaging C-arm cover as recited in claim 1, wherein at least a portion of the enclosure is collapsible.

6. The sterile X-ray imaging C-arm cover as recited in claim 5, wherein the enclosure is configured to expand upon insertion of the portion of the C-arm into the envelope formed by the enclosure.

7. The sterile X-ray imaging C-arm cover as recited in claim 1, wherein the enclosure is rigid in shape.

8. The sterile X-ray imaging C-arm cover as recited in claim 1, wherein the width of the front wall is fixed at a width greater than a width of the portion of the C-arm.

9. The sterile X-ray imaging C-Arm cover as recited in claim 1, wherein the width of the front wall is variable.

10. The sterile X-ray imaging C-arm cover as recited in claim 1, wherein the bottom wall has a height equal to the desired width of the two sidewalls.

11. The sterile X-ray imaging C-arm cover as recited in claim 1, wherein the one or more securing mechanisms are removable from the medical table.

12. The sterile X-ray imaging C-arm cover as recited in claim 1, wherein the front wall and the bottom wall have a monolithic construction.

* * * * *